(12) United States Patent
Pronk

(10) Patent No.: US 9,187,481 B2
(45) Date of Patent: Nov. 17, 2015

(54) (2S)-2-[[4-[(1R)-1-[(2,4-DIAMINOPTERIDIN-6-YL)METHYL]BUT-3-YNYL]BENZOYL]AMIN]PENTANEDIOIC ACID FOR THE TREATMENT OF INFLAMMATORY DISORDERS

(71) Applicant: Allos Therapeutics, Inc., Westminster, CO (US)

(72) Inventor: Gijsbertus J. Pronk, Westminster, CO (US)

(73) Assignee: Allos Therapeutics, Inc., Westminster, CO (US)

( * ) Notice: Subject to any disclaimer, the term of this patent is extended or adjusted under 35 U.S.C. 154(b) by 0 days.

(21) Appl. No.: 14/467,812

(22) Filed: Aug. 25, 2014

(65) Prior Publication Data

US 2014/0364437 A1    Dec. 11, 2014

Related U.S. Application Data

(60) Division of application No. 13/800,593, filed on Mar. 13, 2013, now Pat. No. 8,835,433, which is a continuation of application No. 12/717,736, filed on Mar. 4, 2010, now abandoned.

(60) Provisional application No. 61/300,615, filed on Feb. 2, 2010.

(51) Int. Cl.
C07D 475/08    (2006.01)

(52) U.S. Cl.
CPC .................. C07D 475/08 (2013.01)

(58) Field of Classification Search
CPC ...................................................... C07D 475/08
USPC ............................................................ 544/260
See application file for complete search history.

(56) References Cited

U.S. PATENT DOCUMENTS

| | | | |
|---|---|---|---|
| 4,393,064 | A | 7/1983 | DeGraw, Jr. et al. |
| 4,433,147 | A | 2/1984 | DeGraw, Jr. et al. |
| 4,652,533 | A | 3/1987 | Jolley |
| 4,843,155 | A | 6/1989 | Chomczynski |
| 5,066,828 | A | 11/1991 | Bey et al. |
| 5,286,726 | A | 2/1994 | Bey et al. |
| 5,354,751 | A | 10/1994 | DeGraw, Jr. et al. |
| 5,374,726 | A | 12/1994 | DeGraw |
| 5,981,592 | A | 11/1999 | Wechter et al. |
| 6,028,071 | A * | 2/2000 | Sirotnak et al. ............... 514/249 |
| 6,100,411 | A | 8/2000 | Ojima |
| 6,323,205 | B1 | 11/2001 | Sirotnak et al. |
| 6,410,696 | B1 | 6/2002 | DaValian et al. |
| 7,622,470 | B2 | 11/2009 | O'Connor et al. |
| 7,939,530 | B2 | 5/2011 | O'Connor et al. |
| 8,299,078 | B2 | 10/2012 | O'Connor et al. |
| 2004/0028607 | A1 | 2/2004 | Verdin et al. |
| 2005/0148029 | A1 | 7/2005 | Buechler et al. |
| 2005/0267117 | A1 | 12/2005 | O'Connor et al. |
| 2006/0121085 | A1 | 6/2006 | Warren et al. |
| 2007/0093969 | A1 | 4/2007 | Mendrick et al. |
| 2008/0058280 | A1 | 3/2008 | O'Connor et al. |
| 2008/0108091 | A1 | 5/2008 | Hennessy et al. |
| 2011/0190305 | A1 | 8/2011 | Pronk |
| 2013/0143891 | A1 | 6/2013 | Pronk |
| 2013/0178441 | A1 | 7/2013 | Fruchtman |
| 2013/0197004 | A1 | 8/2013 | Pronk |

FOREIGN PATENT DOCUMENTS

| | | |
|---|---|---|
| WO | WO 98/02163 | 1/1998 |
| WO | WO 03/045429 | 12/2003 |
| WO | WO 2005/117891 | 12/2005 |
| WO | WO 2005/117892 | 12/2005 |
| WO | WO 2011/096947 | 8/2011 |
| WO | WO 2011/153368 | 12/2011 |
| WO | WO 2012/021392 | 2/2012 |

OTHER PUBLICATIONS

Akutsu et al., (2002) "Schedule-dependent Synergism and Antagonism Between Methotrexate and Cytarabine Against Human Leukemia Cell Lines in Vitro" Leukemia 16:1808-1817.

Allos Therapeutics, Inc., "Results Reproted at the American Society of Hematology Annual Meeting Affirm Impressive Activity of Allos Therapeutics' Novel Antifolate PDX in Patients with Peripheral T-Cell Lymphoma." Dec. 11, 2006 (Press Release).

Allos Therapeutics, Inc., "Allos Therapeutics Reports Interim Response and Safety Data from Pivotal Phase 2 Propel Trial" May 15, 2008 (Press Release).

Arango et al. (2009) Clinical Lung Cancer 10(2):91-98 "Second-Line Therapy for Non-Small-Cell Lung Cancer".

Assaraf, Yehuda G. (2007) "Molecular Basis of Antifolate Resistance" Cancer Metastasis Rev. 26:153-181 Springer.

Au et al. (2000) "Aggressive subcutaneous panniculitis-like T-cell lymphoma: complete remission with fludarabine, mitoxantrone and dexamethasone" British Journal of Dermatology, 143:408-410.

Ausubel, et al., "Current Protocols in Molecular Biology" 1987, Current Protocols, vol. 2.

Awar et al., (2007) "Treatment of Transformed Mycosis Fungoides with Intermittent Low-Dose Gemcitabine" Oncologly 73:103-135, Department of Internal Medicine.

Azzoli et al., (2007) "A Phase 1 Study of Pralatrexate in Combination with Paclitaxel or Docetaxel in Patients with Advance Solid Tumors" Clin. Cancer Res. 13(9):2692-2698.

Barberio et al., (2007) "Transformed Mycosis Fungoides: Clinicopathological Features and Outcome" British Journal of Dermatology 157:284-289, British Association of Dermatologists.

Barredo et al., (1994) "Differences in Constitutive and Post-Methotrexate Folylpolyglutamate Synthetase Activity in B-Lineage and T-Lineage Leukemia" Blood 84(2)564-569.

(Continued)

*Primary Examiner* — Douglas M Willis
(74) *Attorney, Agent, or Firm* — Swanson & Bratschun, L.L.C.

(57) ABSTRACT

The present invention relates to diastereomers of 10-propargyl-10-deazaaminopterin, compositions comprising optically pure diastereomers of 10-propargyl-10-deazaaminopterin, in particular the two (R,S) diastereomers about the C10 position, specifically, diastereomers (2S)-2-[[4-[(1S)-1-[(2,4-diaminopteridin-6-yl)methyl]but-3-ynyl]benzoyl]amino]pentanedioic acid and/or (2S)-2-[[4-[(1R)-1-[(2,4-diaminopteridin-6-yl)methyl]but-3-ynyl]benzoyl]amino]pentanedioic acid. Methods of preparation of these diastereomers, compositions containing them, and their use for the treatment of conditions related to inflammatory disorders and cancer are also disclosed.

8 Claims, 1 Drawing Sheet

(56) References Cited

OTHER PUBLICATIONS

Bekkenk et al., (2003) "Peripheral T-Cell Lymphomas Unspecified Presenting in the Skin: Analysis of Prognostic Factors in a Group 82 Patients" Blood 102(6):2213-2219, The American Society of Hematology.

Burg et al., (2005) "WHO/EORTC Classification of Cutaneous Lymphomas 2005: Histological and Molecular Aspects" Journal of Cutaneous Pathology 32:647-674, Blackwell Munksgaard.

Burg et al., (2007) "Cutaneous Lymphomas Current and Future Concepts" J. Egypt Wom. Dermatol. Soc. 4(1):1-23.

Cadman et al., (1979) "Mechanism of Synergistic Cell Killing When Methotrexate Precedes Cytosine Arabinoside" J. Clin. Invest. 64:788-797.

Chau et al., (2002) "Gemcitabine and It's Combinations in the Treatment of Malignant Lymphoma" Clinical Lymphoma 3:97-104.

Cheson et al., (1999) "Report of an International Workshop to Standardize Response Criteria for Non-Hodgkin's Lymphomas" 17(4):1244-1253, Journal of Clinical Oncology.

Coiffier et al. (Jun. 15-18, 2011) International Conference of Myeloma and Lymphoma, Lugano, Switzerland, Poster: "Pralatrexate Reverses the Trend to Progressive Resistance in Patients With Relapsed/Refractory Peripheral T-Cell Lymphoma (PTCL)".

Connors et al., (2002) "Lymphoma of the Skin" Hematology 263-282, American Society of Hematology.

Courtenay et al. (1980) Nature 283:666-668, "Immunisation against heterologous type II collagen induces arthritis in mice".

DeGraw et al. (1986) J. Med. Chem. 29(6):1056-1061, "Synthesis and biological activity of resolved carbon-10 diastereomers of 10-methyl- and 10-ethyl-10-deazaminopterin".

DeGraw et al. (1993) J. Med. Chem. 36:2228-2231, "Synthesis and Antitumor Activity of 10-Propargyl-10-deazaaminopterin".

DeGraw et al. (1995) Current Medicinal Chem. 2:630-653, "New Analogs of Methotrexate in Cancer and Arthritis".

DeGraw et al., (1982) "Synthesis and Antitumor Activity of 10-Alkyl-10-deazaminopterins. A convenient Synthesis of 10-Deazaaminopterin." J. Med. Chem. 25:1227-1230, American Chemical Society.

Diamandidou et al., (1998) "Transformation of Mycosis Fungoides/Sezary Syndrome: Clinical Characteristics and Prognosis" Blood 92:1150-1159.

Diddens et al., (1983) Patterns of Cross-Resistance to the Antifolate Drugs Trimetrexate, Metoprine, Homofolate, and CB3717 in Human Lymphoma and Osteosarcoma Cells Resistant to Methotrexate Cancer Research 43:5286-5292.

Dmitrovsky et al., (1987) "Cytologic Transformation in Cutaneous T-Cell Lymphoma: A Clinicopathologic Entity Associated with Poor Prognosis" Journal of Clinical Oncology 5(2):208-215, The American Society of Clinical Oncology.

Dörwald (2005) Weinheim: WILEY-VCH Verlag GmbH & Co. KGaA "Side Reactions in Organic Synthesis: A Guide to Successful Synthesis Design" Preface.

Food and Drug Administration (Sep. 24, 2009) "NDA #022468" documents—Part 1 and Part 2.

Folotyn (pralatrexate injection) (Sep. 24, 2009) Package Insert: "Highlights of Prescribing Information" 16 pages [online] <URL:http://www.accessdata.fda.gov/drugsatfda_docs/label/2009/022468lbl.pdf>.

Fotoohi, et al., (2004) "Disparate Mechanisms of Antifolate Resistance Provoked by Methotrexate and its Metabolite 7-Hydroxymethotrexate in Leukemia cells: Implications for Efficacy of Methotrexate Therapy" Blood 104:4194-4201 American Society of Hematology.

Fouchard et al., (1998) "Cutaneous T cell lymphomas: mycosis fungoides, Sezary syndrome and HTLV associated adult T cell leukemia (ATL) in Mali, West Africa: a clinical, pathological and immunovirological study of 14 cases and a review of the African ATL cases." Leukemia, 12:578-585.

Fry et al., (1987) "Biological and Biochemical Properties of New Anticancer Folate Antagonists" Cancer and Metastasis Reviews 5:251-270, Martinus Nijoff Publishers, Boston.

Fury et al., (2006) "A Phase I Clinical Pharmacologic Study of Pralatrexate in Combination of with Probenecid in Adults with Advance Solid Tumors" Cancer Chemother Pharmacol. 57:671-677, Springer-Vertag.

Galpin et al., (1997) "Differences in Folylpolyglutamate Synthetase and Dihydrofolate Reductase Expression in Human B-Lineage Versus T-Lineage Leukemic Lymphoblasts: Mechanisms for Lineage Differences in Methotrexate Polyglutamylation and Cytotoxicity" Molecular Pharmacology 52:155-163, The American Society for Pharmacology and Experimental Therapeutics.

Giaccone et al. (1996) The Oncologist 1:82-87, "Drug Resistance".

Gangjee et al., (1995) "Effect of Bridge Region Variation on Antifolate and Antitumor Activity of Classical 5-Substitued 2,4-Diaminofuro [2,3-d] Pyrimidines" J. Med. Chem. 38:3798-3805, American Chemical Society.

Giovanetti et al., "Synergistic Cytotoxicity and Pharmacogenetics of Gemcitabine and Pemetrexed Combination in Pancreatic Cancer Cell Lines" Clinical Cancer Research (2004) vol. 10 pp. 2936-2943.

Girardi et al., (2004) "The Pathogenesis of Mycosis Fungoides" The New England Journal of Medicine 350(19):1978-1988 , Massachusetts Medical Society.

Gisselbrecht et al. (1998) "Prognostic Significance of T-Cell Phenotype in Aggressive Non-Hodgkin's Lymphomas" Blood 92(1):76-82, The American Society of Hematology.

Goy et al. (Dec. 10-13, 2011) $53^{rd}$ ASH Annual Meeting and Exposition , San Diego, California, Paper: "Pralatrexate Is Effective in Patients with Relapsed or Refractory Peripheral T-Cell Lymphoma (PTCL) with Prior Ifosfamide, Carboplatin, and Etoposide (ICE)—Based Regimens".

Grant et al., "Phase II Trials in Small-Cell Lung Cancer: Shouldn't We Be Doing Better?", Journal of the National Cancer Institute, (1992) vol. 84, 1058-1059.

Grenzebach et al., (2001) "Favorable Outcome for Children and Adolescents with T-cell Lymphoblastic Lymphoma with an Intensive All-type Therapy Without Local Radiotherapy" Ann. Hematol. 80:B73-B76, Springer-Verlag.

Hallermann et al., (2007) "Regulatory T-Cell Phenotype in Association with Large Cell Transformation of Mycosis Fungoides" European Journal of Haematology78:260-263, Blackwell Munksgaard.

Haynes, et al., (1968) "Therapy of Mycosis Fungoides" Progress in Dermatology 3:1-5, Dermatology Foundation.

Holm et al., (1980) "High and Low Affinity Binding of Folate to Proteins in Serum of Pregnant Women" Biochimica et Biophysica Acta 629:539-545, Elsevier/North-Holland Biomedical Press.

Hoovis et al., (1973) "Enhancement of the Antiproliferative Action of 1-β-D-Arabinofuranosylcytosine by Methotrexate in Murine Leukemic Cells (L5178Y)" Cancer Research 33:521-525.

Howard et al., (2000) "Mycosis Fungoides: Classic Disease and Variant Presentations" 19(2):91-99, Departments of Pathology and Dermatology, Seminars in Cutaneous Medicine and Surgery.

Huennekens et al., (1994) "The Methotrexate Story: A Paradigm for Development of Cancer Chemoterapeutic Agents" Advan. Enzyme Regul. 34:397-419, Elsevier.

Hum et al., (1996) "Folate, antifolates, and folate analogs in Pediatric Oncology", Invest. New Drugs 14:101-111.

International Search Report and Written Opinion prepared by the U.S. Patent and Trademark Office as International Searching Authority for PCT International Patent Application PCT/US10/26262 mailed Apr. 23, 2010, 19 pages.

International Search Report and Written Opinion prepared by the U.S. Patent and Trademark Office as International Searching Authority for PCT International Patent Application No. PCT/US08/73490, mailed Nov. 10, 2008, 10 pages.

International Search Report and Written Opinion for PCT/US11/38953, mailed Sep. 12, 2011, 34 pages.

International Search Report and Written Opinion for PCT/US11/46711, mailed Dec. 20, 2011, 6 pages.

Janeway-Travers. "Immunobiology: the immune system in health and disease" 1996, 2nd edition.

(56) References Cited

OTHER PUBLICATIONS

Jordan (2003) Nature Reviews: Drug Discovery 2:205-213 "Tamoxifen: A Most Unlikely Pioneering Medicine".
Kamarashev et al., (2007) "Mycosis Fungoides—Analysis of the Duration of Disease Stages in Patients Who Progress and the Tim Point of High-Grade Transformation," International Journal of Dermatology 46:930-935; The International Society of Dermatology.
Kamen (1997) "Folate and Anti-folate Pharmacology" Sem. in Oncol. 24(5):S18-30 to S18-39.
Khokar, et al. (2001) Clinical Cancer Research 7:3199-3205, "Experimental Therapeutics with a New 10-Deazaaminopterin in Human Mesothelioma: Further Improving Efficacy through Structural Design, Pharmacologic Modulation at the Level of MRP ATPases, and Combined Therapy with Platinums".
Krug et al, (2003) "10-propargyl-10-deazaaminopterin: An Antifolate with Activity in Patients with Previously Treated Non-small Cell Lung Cancer" Clinical Cancer Research 9:2072-2078.
Krug et al., (2000) "Phase I and Pharmacokinetic Study of 10-Propargyl-10-deazaaminopterin, a New Antifolate" Clincial Cancer Research 6:3493-3498.
Krug et al., (2007) "Phase II Trial of Pralatrexate (10-Propargyl-10-deazaaminoptrein, PDX) in Patients with Unresectable Malignant Pleural Mesothelioma" Journal of Thoracic Oncology, 2(4):317-320.
Leclerc et al., (2006) "Analysis of Folylpoly-γ-glutamate Synthetase Gene Expression in Human B-precursor ALL and T-lineage ALL Cells" BMC Cancer 6(132):1-12, BioMed Central.
Li et al. (2007) Clin Cancer Res 13:3413-3422 "Schedule-Dependent Cytotoxic Synergism of Pemetrexed and Erlotinib in Human Non-Small Cell Lung Cancer Cell".
Liang et al., (1992) "Intensive chemotherapy for peripheral T-cell lymphomas." Hematological Oncology, 10:155-161.
Longo-Sorbello et al., (2001) "Current Understanding of Methotrexate Pharmacology and Efficacy in Acute Leukemias. Use of Newer Antifolates in Clinical Trials" Hematologica 86:121-127, Trends in Hematology.
Lundin et al., (2004) "Therapy for Mycosis Fungoides" Current Treatment Options in Oncology 5:203-214, Current Science Inc.
Malik et al. (2010) Clin Cancer Res. 16(20):4921-4927 "Folotyn (pralatrexate injection) for the treatment of patients with relapsed or refractory peripheral T-cell lymphoma: U.S. Food and Drug Administration drug approval summary".
Mangone et al. (Dec. 10-13, 2011) 53rd ASH Annual Meeting and Exposition, San Diego, California, Abstract: "Pralatrexate Has Potent Activity Against Multiple Myeloma In Vitro and In Vivo, and Activity Correlates with Tumor RFC-1 and DHFR Expression".
Matsuo et al. (2001) "Association between polymorphisms of folate and methionine-metabolizing enzymes and susceptibility to malignant lymphoma" Blood, 97(10):3205-3209.
Mayne Pharma USA (2005) Methotrexate Injection, USP, Preservative Free: Package Insert, 1-26.
McDonald et al., (1974) "Cutaneous Uses of the Antiproliferative Drugs" Clinical Pharmacology and Therapeutics, 16(5):934-939.
McGuire, "Anticancer Antifolates: Current Status and Future Directions", (2003) in Current Pharmaceutical Design, 9(31), pp. 2593-2613.
Mercadal et al., (2008) "Intensive Chemotherapy (high-dose CHOP/ESHAP regimen) Followed by Autologous Stem-cell Transplantation in Previous Untreated Patients with Peripheral T-cell Lymphoma" Annals. of Oncology 19:958-963, Oxford University.
Moccio et al., (1984) "Similar Specificity of Membrane Transport for Folate Analogues and Their Metabolites by Murine and Human Tumor Cells" A Clinically Directed Laboratory Study Cancer Research 44:352-357.
Molina et al., (2008) "Pralatrexate, a Dihydrofolate Reductase Inhibitor for the Potential Treatment of Several Malignancies" IDrugs 11(7):508-521, Drug Profile.
Montgomery et al., (1979) "Analogues of Methotrexate", J. Med. Chem., 22(7):862-868.
Mould et al. (2009) Clinical Pharmacology & Therapeutics 86(2):190-196 "A Population Pharmacokinetic and Pharmacodynamic Evaluatioin of Pralatrexate in Patients With Relapsed or Refractory Non-Hodgkin's or Hodgkin's Lymphoma".
Nair et al., (1988) "Synthesis and Biological Evaluation of Poly-γ-glutamyl Metabolites of 10-Deazaaminopterin and 10-Ethyl-10-deazaaminopterin" J. Med. Chem. 181-185, American Chemical Society.
O'Connor et al., (2005) "Pralatrexate (10-propargyl-10-deazaaminopterin (PRX)), a Novel Antifolate, Effects Durable Complete Remissions (CR) in Patients with a Diversity of Drug Resistant T-Cell Lymphomas with Minimal Toxicity" Blood 106: Abstract 2678, American Society of Hematology.
O'Connor et al., (2006) "Pralatrexate (PDX) Produces Durable Complete Remissions in Patients with Chemotherapy Resistant Precursor and Peripheral T- Cell Lymphomas: Results of the MSKCC Phase I/II Experience" Blood 108: Abstract 400, American Society of Hematology.
O'Connor et al., (2006) "Pralatrexate: An Emerging New Agent with Activity in T-Cell Lymphomas" Current Opinion in Oncology18:591-597, Lippincott Williams & Wilkins.
O'Connor et al., (2007) "A Phase '2-1-2' Study of Two Different Doses and Schedules of Pralatrexate, a High Affinity Substrate for the Reduced Folate Carrier (rfc-1), in Patients with Relapsed or Refractory Lymphoma Reveals Marked Activity in T-Cell Malignancies" AACR—NCI-EORTC International Conference: Molecular Targets and Cancer Therapeutics, Oct. 22-26, 2006; San Francisco, CA, poster.
O'Connor et al., (2007) "Pralatrexate, a Novel Class of Antifol with High Affinity for the Reduced Folate Carrier Type 1, Produces Marked Complete and Durable Remissions in a Diversity of Chemotherapy Refactory Cases of T-Cell Lymphoma" British Journal of Haematology 139:425-428, Blackwell Publishing Ltd.
O'Connor, O. (2005) "Developing New Drugs for the Treatment of Lymphoma" European Journal of Haematology 75(Supp 66):150-158, Blackwell Munksgaard.
O'Connor et al. (2011) Journal of Clinical Oncology 29(9):1182-1189 "Pralatrexate in patients with relapsed or refractory peripheral T-Cell lymphoma (PTCL): results from the pivotal PROPEL study".
Olsen et al., (2007) "Revisions to the Staging and Classification of Mycosis Fungoides and Sézary Syndrome: A Proposal of the Intenational Society for Cutaneous Lymphomas (ISCL) and the Cutaneous Lymphoma Task Force of the European Organization of Research and Treatment of Cancer (EORTC)" Blood 110(6):1713-1722, The American Society of Hematology.
Paulli et al., (2004) "Cutaneous T-Cell Lymphoma (including rare subtypes). Current concepts. II" Haematologica 89:1372-1388, Malignant Lymphomas.
Prochazkova et al., (2005) "Large Cell Transformation of Mycosis Fungoides: Tetraploidization Within Skin Tumor Large Cells" Cancer Genetics and Cytogenetics 163:1-6.
Quereux et al., (2008) "Prospective Multicenter Study of Pegylated Liposomal Doxorubicin Treatment in Patients with Advanced or Refractory Mycosis Fungoides or Sézary Syndrome" Arch. Dermatology 144(6):727-733.
Rezania et al. (2007) "The Diagnosis, Magangement, and Role of Hematopoietic Stem Cell Transplantation in Aggressive Peripheral T-Cell Neoplasms" Cancer Control 14(2):151-159.
Rizvi et al., (2006) "T-Cell Non-Hodgkin Lymphoma" Blood 107(4):1255-1264, The American Society of Hematology.
Rodriguez-Abreu et al. (2008) "Peripheral T-cell Lymphomas, unspecified (or not otherwise specified): a review." Hematol. Oncol., 26:8-20.
Rosen et al. (2006) "Primary Cutaneous T-Cell Lymphomas" pp. 323-330, American Society of Hematology.
Rots et al., (1999) "Role of Folylpolyglutamate Synthetase and Folylpolyglutamate Hydrolase in Methotrexate Accumulation and Polyglutamylation in Childhood Leukemia" Blood 93:1677-1683, The American Society of Hematology.
Rots et al., (2000) "mRNA Expression Levels of Methotrexate Resistance-Related Proteins in Childhood Leukima as Determined by a Standardized Competitive Template-Based RT-PCR Method" Leukemia 14:2166-2175, Macmillian Publishers Ltd.
Rueda et al. (2009) Clin Transl Oncol 11:215-220 "Pralatrexate, a new hope for aggressive T-cell lymphomas?".

(56) References Cited

OTHER PUBLICATIONS

Rumberger et al., (1990) "Differing Specificities for 4-Aminofolate Analogues of Folylpolyglutamyl Synthetase from Tumors and Proliferative Intestinal Epithelium of the Mouse with Significance for Selective Antitumor Action" Cancer Research 50:4639-4643.

Salhany et al., (1988) "Transformation of Cutaneous T Cell Lymphoma to Large Cell Lymphoma" American Journal of Pathology 132(2):265-277, American Association of Pathologists.

Sambrook et al., (1989) "Molecular Cloning" A Laboratory Manual, Cold Springs Harbor, Second Edition, sections 8.9-8.10.

Samuels et al., (1985) "Similar Differential for Total Polyglutamylation and Cytotoxicity Among Various Folate Analogues in Human and Murine Tumor Cells in Vitro" Cancer Research 45:1488-1495, Presented in part at the 74th Annual Meeting of the American Association for Cancer Research.

Samuels et al., (1986) "Hydrolytic Cleavage of Methotrexate γ-Polyglutamates by Folylpolyglutamyl Hydrolase Derived from Various Tumors and Normal Tissues of the Mouse" Cancer Research 46:2230-2235.

Sarris et al., (2002) "Trimetrexate in Relapsed T-Cell Lymphoma With Skin Involvement" Journal of Clinical Oncology 20(12):2876-2880, The American Society of Clinical Oncology.

Savage et al., (2004) "Characterization of Peripheral T-Cell Lymphomas in a Single North American Institution by the WHO Classification" Annals of Oncology 15:1467-1475.

Savage, (2005) "Aggressive Peripheral T-Cell Lymphomas (Specified and Unspecified Types)" Hematology, pp. 267-277, American Society of Hematology.

Scott, et al., (1968) "Therapy of Mycosis Fungoides Lymphoma" Skin Cancer Panel, J.B. Lippincott Company, pp. 553-557.

Serajuddin (2007) Advanced Drug Delivery Reviews 59:603-616 "Salt Formation to Improve Drug Solubility".

Shustov et al. (2010) Journal of Clinical Oncology, ASCO Annual Meeting Proceedings 28(15):Abstract No. 8054 "Pralatrexate in patients with relapsed/refractory peripheral T-cell lymphoma (PTCL): Relationship between response and survival".

Shustov et al. (Aug. 15-19, 2011) Pan Pacific Lymphoma Conference, Koloa, Hawaii, Poster: "Pralatrexate: An Effective Single-Agent, Second-Line Treatment in Patients With Relapsed/Refractory Peripheral T-Cell Lymphoma (PTCL) Following Failure of Cyclophosphamide/Doxorubicin/Vincristine/Prednisone (CHOP)".

Shustov et al. (Aug. 15-19, 2011) Pan Pacific Lymphoma Conference, Koloa, Hawaii, Presentation Outline: "Pralatrexate: An Effective Single-Agent, Second-Line Treatment in Patients With Relapsed/Refractory Peripheral T-Cell Lymphoma (PTCL) Following Failure of Cyclophosphamide/Doxorubicin/Vincristine/Prednisone (CHOP)".

Siegel et al., (2000) "Primary Cutaneous T-Cell Lymphoma: Review and Current Concepts" Journal of Clinical Oncology 18(15):2908-2925, American Society of Clinical Oncology.

Silvestri et al., "Targeted Therapy for the Treatment of Advanced Non-small Cell Lung Cancer: A Review of the Epidermal Growth Factor Receptor Antagonist" Chest Journal (2005) 128:3975-3984.

Sirotnak et al. (2000) Clinical Cancer Research 6:3705-3712, "Co-administration of probenecid, an inhibitor of a cMOAT/MRP-like plasma membrane ATPase, greatly enhanced the efficacy of a new 10-deazaaminopterin against human solid tumors in vivo".

Sirotnak et al., (1979) "Strereospecificity at Carbon 6 of Formyltetrahydrofolate as a Competitive Inhibitor of Transport and Cytotoxicity of Methotrexate in Vitro" Biochemical Pharmacology 28:2993-2997, Pergamon Press Ltd., Great Britain.

Sirotnak et al., (1984) "New Folate Analogs of the 10-deaza-aminopterin Series Basis for Structural Design and Biochemical and Pharmacologic Properties" Cancer Chemotherapy Pharmacology 12:18-25, Springer-Verlag.

Sirotnak et al., (1988) "Analogs of Tetrahydrofolate Directed at Folate-dependent Purine Biosynthetic Enzymes. Characteristics of Mediated Entry and Transport-Related Resistance in L1210 Cells for 5, 10-dideazatetrahydrofolate and two 10-alkyl Derivatives" Biochemical Pharmacology 37(24):4775-4777, Pergamon Press plc., Great Britain.

Sirotnak et al., (1993) "Markedly Improved Efficacy of Edatrexate Compared to Methotrexate in a High-Dose Regimen with Leucovorin Rescue Against Metastatic Murine Solid Tumors" Cancer Research 53:587-591.

Sirotnak et al., (1998) "A New Analogue of 10-Deazaaminopterin with Markedly Enhanced Curative Effects Against Human Tumor Xenografts in Mice" Cancer Chemotherapy Pharmacology 42:313-318, Springer-Verlag.

Skibola et al., (2004) "Polymorphisms and Haplotypes in Folate-Metabolizing Genes and Risk of Non-Hodgkin Lymphoma" Blood 104:2155-2162, www.bloodjournal.org.

Skibola et al., (2007) "Genetic Susceptibility to Lymphoma" Haematologica/The Hematology Journal 92(7):960-969.

Slater, D.N., (2005) "The New World Health Organization-European Organization for Research and Treatment of Cancer Classification for Cutaneous Lymphomas: A Practical Marriage of Two Giants" British Journal of Dermatology 153:874-880, British Association of Dermatologists.

Takimoto (1996) "New Antifolates: Pharmacology and Clinical Applications" Oncologist, 1:68-81.

Teicher et al., "Treatment Regimens Including the Multitargeted Antifolate LY231514 in Human tumor Xenografts" Cinical Cancer Researh (2000) vol. 6 pp. 1016-1023.

Toner et al., (2006) "The Schedule-Dependent Effect of the Novel Antifolate Pralatrexate and Gemcitabine Are Superior to Methotrexate and Cytarabine in Models of Human Non-Hodgkins's Lymphoma" Clin. Cancer Res. 12(3):924-932, www.aacrjournals.org.

Tonkinson et al., "Cell Cycle Modulation by a Multitargeted Antifolate, LY231514, Increases the Cytotoxicity and Antitumor Activity of Gemcitabine in HT29 Colon Carcinoma" Cancer.

Ueda et al., (1986) "Inhibitory Action of 10-Deazaaminopterins and Their Polyglutamates of Human Thymidylate Synthase" Molecular Pharmacology 30:149-153, The American Society for Pharmacology and Experimental Therapeutics.

Vergier et al., (2000) "Transformation of Mycosis Fungoides: Clinicopathological and Prognostic Features of 45 Cases" 95(6):2212-2218.

Vonderheid et. al., (2003) "Treatment Planning in Cutaneous T-Cell Lymphoma" Dermatologic Therapy 16:276-282.

Vrhovac, et al., (2003) "A Novel Antifolate 10-propargyl-10-deazaaminopterin (PDX) Displays Synergistic Effects with Gemcitabine in Non-Hodgkin's Lymphoma Models in Vitro and in Vivo" 45th Annual Meeting of the American Society of Hematology 102(11):288b.

Wang et al., (2001) "PDX, a Novel Antifolate with Potent in Vitro and in Vivo Activity in Non-Hodgkin's Lymphoma" Developmental Hematology and the Program for Molecular Pharmacology and Experimental Therapeutics, Abstract 2565.

Wang et al., (2003) "Activity of a Novel Anti-Folate (PDX, 10-Propargyl-10-Deazaaminopterin) Against Human Lymphoma is Superior to Methotrexate and Correlates with Tumor RFC-1 Gene Expression" Leukemia and Lymphoma 44(6):1027-1035.

Weidmann et al., (2004) "Diagnosis and Actual Therpay Strategies in Peripheral T-Cell Lymphomas: Summary of an International Meeting" Annals of Oncology 15:369-374.

Weinstein (1977) "Diagnosis and Treatment: Drugs Five Years Later: Methotrexate" Annals of Internal Medicine, 86:199-204.

Willemze et al., (2005) "WHO-EORTC Classification for Cutaneous Lymphomas" Blood 105(10):3768-3785, wwww.bloodjournal.org, The American Society of Hematology.

Wright et al., (2003) "Further Studies on the Interaction of Nonpolyglutamatable Aminopterin Analogs with Dihydrofolate Reductase and the Reduced Folate Carrier as Determinants of In Vitro Antitumor Activity" Biochemical Pharmacology 65:1427-1433, Elsevier.

Chinese Search Report in English only for Application No. 2011800385386 dated Dec. 19, 2013.

European Search Report for Application No. 11816854.1 dated Jul. 23, 2013.

(56) References Cited

OTHER PUBLICATIONS

National Comprehensive Cancer Network, www.nccn.org "Non-Hodgkins's Lymphomas" V.3.2008, Apr. 10, 2008.
Starling et al. (1974) Cancer Chemotherapy Reports 58:683-687 "Drug trials in neuroblastoma: cyclophosphamide (NSC-26271) Alone; Vincristine (NSC-67574) plus cyclophosphamide; 6-mercaptopurine (NSC-755) plus 6-methylmercaptopurine riboside (NSC-40774); and Dcy10sinearabinoside (NSC-63878) alone".
European Search Report for Application No. EP11790419.3 dated Jun. 18, 2013.
Sausville et al. "Contributions of Human Tumor xenografts to Anti-cancer Drug Development" Cancer Research, 2006, vol. 66 pp. 3351-3354.
Johnson et al. "Relationships between drug activity in NCI preclinical in vitro and in vivo models and early clinical trials" British J. of Cancer, 2001, 84(10): 1424-1431.
Allos, Inc. (2009) *Folotyn: Highlights of Prescribing Information*. Retrieved from <http://www.accessdata.fda.gov/drugsatfda_docs/label/2009/022468lb1.pdf> on Jul. 29, 2015.
Zelenetz, A. et al. (2011) "Non-Hodgkin's Lymphomas: Clinical Practice Guidelines in Oncology", *JNCCN—Journal of the National Comprehensive Cancer Network* vol. 9 No. 5. Retrieved from <http://www.jnccn.org/content/9/5/484.full.pdf> on Jul. 29, 2015.

* cited by examiner

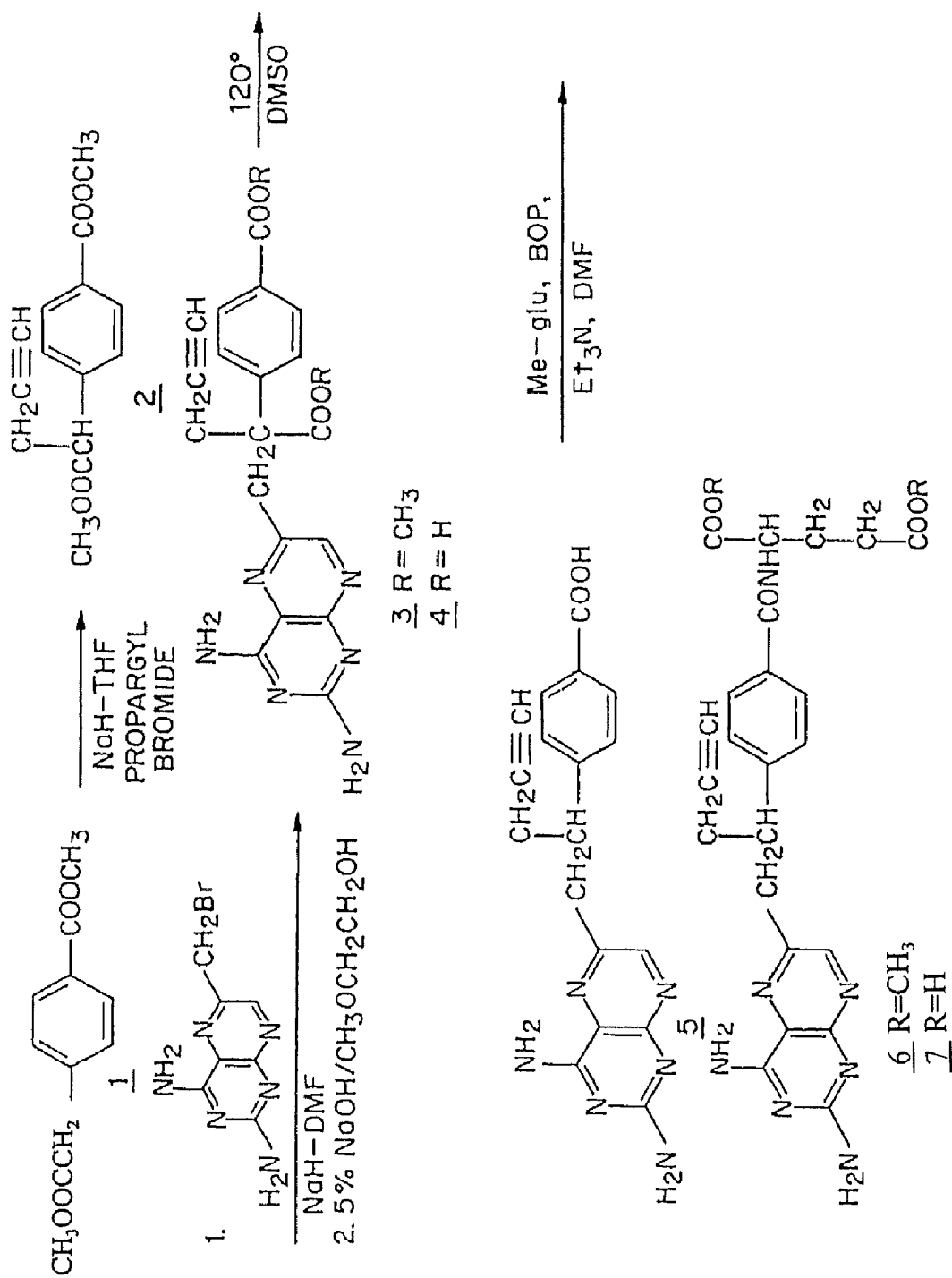

(2S)-2-[[4-[(1R)-1-[(2,4-DIAMINOPTERIDIN-6-YL) METHYL]BUT-3-YNYL]BENZOYL]AMIN] PENTANEDIOIC ACID FOR THE TREATMENT OF INFLAMMATORY DISORDERS

RELATED APPLICATIONS

This application is a divisional of U.S. patent application Ser. No. 13/800,593, filed Mar. 13, 2013, entitled "Optically Pure Diastereomers of 10-Propargyl-10-Deazaminopterin and Methods of Using Same," which is a continuation of U.S. patent application Ser. No. 12/717,736, now abandoned, filed Mar. 4, 2010, entitled "Optically Pure Diastereomers of 10-Propargyl-10-Deazaminopterin and Methods of Using Same," which application claims the benefit of U.S. Provisional Patent Application Ser. No. 61/300,615, filed Feb. 2, 2010, which are hereby incorporated by reference in their entireties.

TECHNICAL FIELD

The present invention relates to compounds and compositions comprising variant forms of 10-propargyl-10-deazaminopterin and use thereof in methods to treat cancer and inflammatory disorders.

BACKGROUND OF THE INVENTION

10-Propargyl-10-deazaminopterin (encompassing "10-propargyl-10-dAM," "pralatrexate," "racemic PDX," "(2S)-2-[[4-[(1RS)-1-[(2,4-diaminopteridin-6-yl)methyl]but-3-ynyl]benzoyl]amino]pentanedioic acid," "(2RS)-2-[[4-[(1RS)-1-[(2,4-diaminopteridin-6-yl)methyl]but-3-ynyl]benzoyl]amino]pentanedioic acid," and "PDX"), is a compound which has been tested and found useful in the treatment of cancer. In its racemic form, (2S)-2-[[4-[(1RS)-1-[(2,4-diaminopteridin-6-yl)methyl]but-3-ynyl]benzoyl]amino]pentanedioic acid has been approved by the U.S. Food and Drug Administration (FDA) as a treatment for relapsed and refractory peripheral T-cell lymphoma. (2S)-2-[[4-[(1RS)-1-[(2,4-diaminopteridin-6-yl)methyl]but-3-ynyl]benzoyl]amino]pentanedioic acid is also being investigated for use in lymphoma, lung cancer, bladder cancer, and breast cancer.

This compound, which has the structure shown in FIG. 1, was originally disclosed by DeGraw et al., "Synthesis and Antitumor Activity of 10-Propargyl-10-deazaminopterin," J. Med. Chem. 36: 2228-2231 (1993) and shown to act as an inhibitor of the enzyme dihydrofolate reductase ("DHFR") and as an inhibitor of growth in the murine L1210 cell line. In addition, some results were presented for the antitumor properties of the compound using the E0771 murine mammary tumor model.

U.S. Pat. No. 6,028,071 and PCT Publication No. WO 1998/02163, disclose that highly purified PDX compositions when tested in a xenograft model have efficacy against human tumors. Subsequent studies with PDX have shown that it is useful on its own and in combinations with other therapeutic agents. For example, Sirotnak et al., Clinical Cancer Research Vol. 6, 3705-3712 (2000) reports that co-administration of PDX and probenecid, an inhibitor of a cMOAT/MRP-like plasma membrane ATPase, greatly enhances the efficacy of PDX against human solid tumors. PDX and combinations of PDX with platinum based chemotherapeutic agents have been shown to be effective against mesothelioma. (Khokar, et al., Clin. Cancer Res. 7: 3199-3205 (2001). Co-administration with gemcitabine (Gem), for treatment of lymphoma, has been disclosed in WO/2005/117892 (Combinations of PDX with taxols are disclosed to be efficacious in U.S. Pat. No. 6,323,205. PDX has also shown to be effective for treatment of T-cell lymphoma, see U.S. Pat. No. 7,622,470. Other studies have shown a method for assessing sensitivity of a lymphoma to treatment with PDX by determining the amount of reduced folate carrier-1 enzyme (RFC-1) expressed by the sample, wherein a higher level of expressed RFC-1 is indicative of greater sensitivity to 10-propargyl-10-dAM, disclosed in PCT Publication No. WO 2005/117892.

The present invention is directed toward overcoming one or more of the problems discussed above.

SUMMARY OF THE INVENTION

In one embodiment, the present invention includes a substantially pure diastereomer of 10-propargyl-10-deazaminopterin, or a salt thereof, wherein the diastereomer is (2S)-2-[[4-[(1S)-1-[(2,4-diaminopteridin-6-yl)methyl]but-3-ynyl]benzoyl]amino]pentanedioic acid or (2S)-2-[[4-[(1R)-1-[(2,4-diaminopteridin-6-yl)methyl]but-3-ynyl]benzoyl]amino]pentanedioic acid. In one embodiment, the substantially pure diastereomer is (2S)-2-[[4-[(1S)-1-[(2,4-diaminopteridin-6-yl)methyl]but-3-ynyl]benzoyl]amino]pentanedioic acid or a salt thereof. In another embodiment, the substantially pure diastereomer is (2S)-2-[[4[(1R)-1-[(2,4-diaminopteridin-6-yl)methyl]but-3-ynyl]benzoyl]amino]pentanedioic acid or a salt thereof. In one aspect, the salt is the hydrochloride salt.

In another embodiment, the present invention includes a pharmaceutical composition, comprising substantially pure (2S)-2-[[4-[(1S)-1-[(2,4-diaminopteridin-6-yl)methyl]but-3-ynyl]benzoyl]amino]pentanedioic acid or salt thereof, or substantially pure (2S)-2-[[4-[(1R)-1-[(2,4-diaminopteridin-6-yl)methyl]but-3-ynyl]benzoyl]amino]pentanedioic acid or salt thereof, and a pharmaceutically acceptable carrier. In some embodiments, the present invention includes a pharmaceutical composition, comprising a pharmaceutically effective amount of substantially pure (2S)-2-[[4-[(1R)-1-[(2,4-diaminopteridin-6-yl)methyl]but-3-ynyl]benzoyl]amino]pentanedioic acid or salt thereof, or substantially pure (2S)-2-[[4-[(1S)-1-[(2,4-diaminopteridin-6-yl)methyl]but-3-ynyl]benzoyl]amino]pentanedioic acid or salt thereof, and a pharmaceutically acceptable carrier. In some embodiments, the pharmaceutical composition of the present invention may be used in a method of treating cancer. The cancer to treat includes prostate cancer, T-cell lymphoma, breast cancer, lung cancer, hematologic malignancies, head and neck cancer, cancer of the gastrointestinal tract, ovarian cancer, and osteosarcoma. In some embodiments, the pharmaceutical composition of the present invention may be used in a method for treating an inflammatory disorder. The inflammatory disorder to treat includes rheumatoid arthritis. In some embodiments, the pharmaceutical composition of the present invention is formulated for oral administration; in other embodiments, the pharmaceutical composition of the present invention is formulated for intravenous administration.

In another embodiment, the present invention includes a method for treating cancer, which includes administering to a mammal in need of said treatment a therapeutically effective amount of a substantially pure diastereomer of 10-propargyl-10-deazaminopterin, or a salt thereof, said diastereomer being (2S)-2-[[4-[(1S)-1-[(2,4-diaminopteridin-6-yl)methyl]but-3-ynyl]benzoyl]amino]pentanedioic acid or (2S)-2-[[4-[(1R)-1-[(2,4-diaminopteridin-6-yl)methyl]but-3-ynyl]benzoyl]amino]pentanedioic acid.

In another embodiment, the present invention includes a method for treating inflammation, comprising administering to a mammal in need of said treatment a therapeutically effective amount of a substantially pure diastereomer of 10-propargyl-10-deazaminopterin, or a salt thereof, said diastereomer being (2S)-2-[[4-[(1S)-1-[(2,4-diaminopteridin-6-yl)methyl]but-3-ynyl]benzoyl]amino]pentanedioic acid or (2S)-2-[[4-[(1R)-1-[(2,4-diaminopteridin-6-yl)methyl]but-3-ynyl]benzoyl]amino]pentanedioic acid. In one embodiment, the substantially pure diastereomer is (2S)-2-[[4-[(1S)-1-[(2,4-diaminopteridin-6-yl)methyl]but-3-ynyl]benzoyl]amino]pentanedioic acid in an amount greater than about 90% by weight of the total amount of 10-propargyl-10-deazaminopterin. In another embodiment, the substantially pure diastereomer is (2S)-2-[[4-[(1R)-1-[(2,4-diaminopteridin-6-yl)methyl]but-3-ynyl]benzoyl]amino]pentanedioic acid in an amount greater than about 90% by weight of the total amount of 10-propargyl-10-deazaminopterin. The methods of the invention further include use of a pharmaceutically acceptable carrier with a substantially pure diastereomer of the present invention. The substantially pure diastereomer of the present invention may be administered orally or intravenously.

In one embodiment, the substantially pure diastereomer of the present invention may be administered weekly. In this embodiment, the substantially pure diastereomer may be administered in an amount of 30 mg/m$^2$ per dose, or in an amount of from 10 to 150 mg/m$^2$ per dose.

In one embodiment, the substantially pure diastereomer of the present invention may be administered biweekly. In this embodiment, the substantially pure diastereomer is administered in an amount of from 100 to 275 mg/m$^2$ per dose, or in an amount of from 10 to 275 mg/m$^2$ per dose.

The substantially pure diastereomer of the present invention may be administered in one or more cycles, each cycle comprising administration once weekly for six weeks in an amount of from 30 to 150 mg/m$^2$ per dose followed by a one week rest.

Optionally, administration of a substantially pure diastereomer of the present invention includes supplementation with folic acid and vitamin $B_{12}$. In one embodiment, the substantially pure diastereomer of the present invention is administered in an amount of from 0.25 to 4 mg/kg per dose.

In one embodiment, the present invention includes use of a substantially pure diastereomer of the present invention in the manufacture of pharmaceutical composition for treating cancer. The present invention also includes use of a substantially pure diastereomers of the present invention in the manufacture of a pharmaceutical composition for treating an inflammatory disorder.

BRIEF DESCRIPTION OF THE DRAWINGS

FIG. 1 shows a synthetic scheme useful in preparing (2S)-2-[[4-[(1RS)-1-[(2,4-diaminopteridin-6-yl)methyl]but-3-ynyl]benzoyl]amino]pentanedioic acid.

DETAILED DESCRIPTION OF THE INVENTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

The present invention relates to methods and compositions effective to treat cancer and inflammatory disorders, comprising diastereomers of pralatrexate. Pralatrexate contains asymmetric centers at the carbon 10 (C10) and carbon 19 (C19) position. In one embodiment, racemic pralatrexate includes an approximately 1:1 racemic mixture of the R- and S-configurations at the C10 chiral center, and ≥98.0% of the S-diastereomer at the C19 chiral center. The two C10 diastereomers of this embodiment are referred to as:

PDX-10a [S-configuration] Chemical name: (2S)-2-[[4-[(1S)-1-[(2,4-diaminopteridin-6-yl)methyl]but-3-ynyl]benzoyl]amino]pentanedioic acid.

PDX-10b [R-configuration] Chemical name: (2S)-2-[[4-[(1R)-1-[(2,4-diaminopteridin-6-yl)methyl]but-3-ynyl]benzoyl]amino]pentanedioic acid.

The racemate, in one embodiment, may be described as (2S)-2-[[4-[(1RS)-1-[(2,4-diaminopteridin-6-yl)methyl]but-3-ynyl]benzoyl]amino]pentanedioic acid, molecular weight: 477.5, molecular formula: $C_{23}H_{23}N_7O_5$, 1:1 mixture of diastereomers at C10.

Formula 1

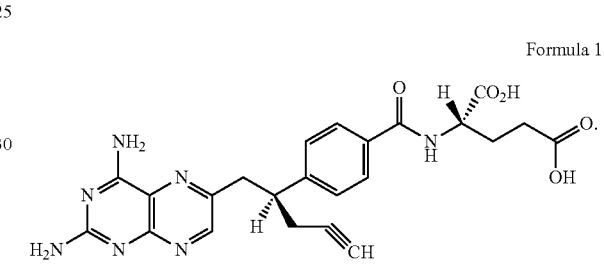

PDX-10a [S-configuration]
Chemical name: (2S)-2-[[4-[(1S)-1-[(2,4-diaminopteridin-6-yl)methyl]but-3-ynyl]benzoyl]amino]pentanedioic acid Formula 2

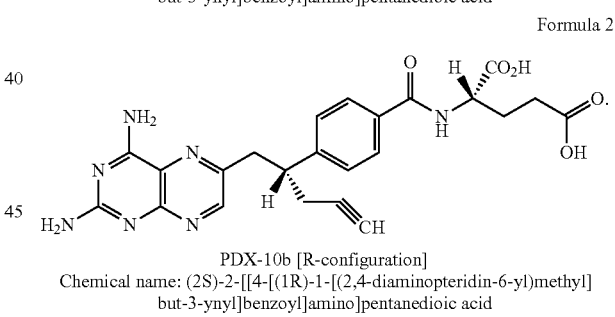

PDX-10b [R-configuration]
Chemical name: (2S)-2-[[4-[(1R)-1-[(2,4-diaminopteridin-6-yl)methyl]but-3-ynyl]benzoyl]amino]pentanedioic acid The C10 diastereomers of PDX, PDX-10a and PDX-10b, have an observed activity that varies based on the cancer cell line; in some cases, the S diastereomer exhibits superior activity versus the racemate, in other cases, it is the R diastereomer that has the superior activity. Differences have also been found in the pharmacokinetics of the diastereomers as compared with each other. It is noted that the folate pathway, by which PDX exerts a substantial portion of its activity, comprises a number of identified enzymes, and may include further, unidentified enzymes. The enzymes in this complex pathway include reduced folate carrier-1 enzyme (RFC-1), dihydrofolate reductase (DHFR), folylpoly-gamma-glutamate synthetase (FPGS), thymidylate synthase (TS), γ-glutamyl hydrolase (GGH), and glycinamide ribonucleotide formyltransferase (GARFT). Art for other deazaminopterins suggests that there is tolerance for variation around the C10 chiral center of the deazaminopterins (e.g., DeGraw et al., 1995, Current Medicinal Chem. 2: 630 and DeGraw et al. 1986, J. Med. Chem. 29 (6): 1056)), which further makes the observed differences in activity between the diastereomers unexpected.

The ability to select a particular diastereomer of PDX that has enhanced activity in a particular cancer relative to the other diastereomer, the racemate, or both, provides a real-world and substantial benefit to a doctor when treating cancer patients. For example, the treating physician would have the multiple options of selecting the racemate of PDX, the PDX-10a [S-configuration], and the PDX-10b [R-configuration]. As set forth in greater detail in the examples herein, PDX-10a and PDX-10b have been tested in model systems for efficacy against various cancer cell lines.

Racemic PDX can be synthesized using the method disclosed in the DeGraw 1993 paper, supra or in Example 7 of DeGraw et al., U.S. Pat. No. 5,354,751, Example 7. U.S. Pat. No. 5,354,751, which is directed to manufacturing PDX, is incorporated by reference herein in its entirety. Racemic PDX may also be synthesized by methods presented in U.S. Pat. No. 6,028,071, especially in Example 1, which example is incorporated by reference herein.

In order to generate PDX-10a and/or PDX-10b, racemic PDX may be synthesized as taught herein and elsewhere, and either the final product or an earlier intermediate product may be subsequently used as a starting material to separate the C10 diastereomers. Alternately, a chiral synthesis may be employed where substantially pure PDX-10a and/or PDX-10b is produced directly from any of a number of starting materials. Chiral columns to separate enantiomers or diastereomers, known in the art, may be employed to separate the diastereomers of the final racemic PDX or an earlier intermediate. Suitable chiral columns for separating the diastereomers include the chiral column CHIRALPAK AD, available from Daicel Chemical Industries Ltd., Japan, using ethanol as the mobile phase.

In one aspect, the present invention provides a substantially pure diastereomer of 10-propargyl-10-deazaminopterin, or a salt, ester, solvate, and/or polymorph thereof, wherein the substantially pure diastereomer is (2S)-2-[[4-[(1S)-1-[(2,4-diaminopteridin-6-yl)methyl]but-3-ynyl]benzoyl]amino]pentanedioic acid or (2S)-2-[[4-[(1R)-1-[(2,4-diaminopteridin-6-yl)methyl]but-3-ynyl]benzoyl]amino]pentanedioic acid. In one embodiment, the substantially pure diastereomer is (2S)-2-[[4-[(1S)-1-[(2,4-diaminopteridin-6-yl)methyl]but-3-ynyl]benzoyl]amino]pentanedioic acid or a salt, ester, solvate, and/or polymorph thereof. In another embodiment, the substantially pure diastereomer is (2S)-2-[[4-[(1R)-1-[(2,4-diaminopteridin-6-yl)methyl]but-3-ynyl]benzoyl]amino]pentanedioic acid or a salt, ester, solvate, and/or polymorph thereof.

The present invention also provides a method for the treatment of cancer in a patient in need thereof, comprising administering to a patient a therapeutically effective amount of a substantially pure diastereomer of 10-propargyl-10-deazaminopterin, or a salt, ester, solvate, and/or polymorph thereof, wherein the substantially pure diastereomer is (2S)-2-[[4-[(1S)-1-[(2,4-diaminopteridin-6-yl)methyl]but-3-ynyl]benzoyl]amino]pentanedioic acid or (2S)-2-[[4-[(1R)-1-[(2,4-diaminopteridin-6-yl)methyl]but-3-ynyl]benzoyl]amino]pentanedioic acid.

In one cancer treatment embodiment, the substantially pure diastereomer is (2S)-2-[[4-[(1S)-1-[(2,4-diaminopteridin-6-yl)methyl]but-3-ynyl]benzoyl]amino]pentanedioic acid or a salt, ester, solvate, and/or polymorph thereof. In another cancer treatment embodiment, the substantially pure diastereomer is (2S)-2-[[4-[(1R)-1-[(2,4-diaminopteridin-6-yl)methyl]but-3-ynyl]benzoyl]amino]pentanedioic acid or a salt, ester, solvate, and/or polymorph thereof. In some embodiments, the substantially pure diastereomer, or salt, ester, solvate, and/or polymorph thereof, of 10-propargyl-10-deazaminopterin is substantially free of 10-deazaminopterin.

"Substantially pure PDX-10a," as used herein means that the amount of PDX-10a is greater than about 90% by weight of the total amount of 10-propargyl-10-dAM; greater than about 91% by weight of the total amount of 10-propargyl-10-dAM; greater than about 92% by weight of the total amount of 10-propargyl-10-dAM; greater than about 93% by weight of the total amount of 10-propargyl-10-dAM; greater than about 94% by weight of the total amount of 10-propargyl-10-dAM; greater than about 95% by weight of the total amount of 10-propargyl-10-dAM, greater than about 96% by weight of the total amount of 10-propargyl-10-dAM; greater than about 97% by weight of the total amount of 10-propargyl-10-dAM; greater than about 98% by weight of the total amount of 10-propargyl-10-dAM, greater than about 98.5% by weight of the total amount of 10-propargyl-10-dAM; greater than about 99% by weight of the total amount of 10-propargyl-10-dAM; greater than about 99.5% by weight of the total amount of 10-propargyl-10-dAM, greater than 99.7% by weight of the total amount of 10-propargyl-10-dAM, greater than about 99.8% by weight of the total amount of 10-propargyl-10-dAM; and greater than about 99.9% by weight of the total amount of 10-propargyl-10-dAM. Similarly, "substantially pure PDX-10b", as used herein means that the amount of PDX-10b is greater than about 90% by weight of the total amount of 10-propargyl-10-dAM; greater than about 91% by weight of the total amount of 10-propargyl-10-dAM; greater than about 92% by weight of the total amount of 10-propargyl-10-dAM; greater than about 93% by weight of the total amount of 10-propargyl-10-dAM; greater than about 94% by weight of the total amount of 10-propargyl-10-dAM; greater than about 95% by weight of the total amount of 10-propargyl-10-dAM, greater than about 96% by weight of the total amount of 10-propargyl-10-dAM; greater than about 97% by weight of the total amount of 10-propargyl-10-dAM; greater than about 98% by weight of the total amount of 10-propargyl-10-dAM, greater than about 98.5% by weight of the total amount of 10-propargyl-10-dAM; greater than about 99% by weight of the total amount of 10-propargyl-10-dAM; greater than about 99.5% by weight of the total amount of 10-propargyl-10-dAM, greater than 99.7% by weight of the total amount of 10-propargyl-10-dAM, greater than about 99.8% by weight of the total amount of 10-propargyl-10-dAM; and greater than about 99.9% by weight of the total amount of 10-propargyl-10-dAM.

Cancers to treat with PDX-10a and/or PDX-10b include, for example, prostate cancer, breast cancer, melanoma, lung cancer, and T-cell lymphoma. For T-cell lymphoma, there are a variety of conditions subject to treatment using the diastereomers of the invention, and they include: (a) lymphoblastic lymphomas in which the malignancy occurs in primitive lymphoid progenitors from the thymus; (b) mature or peripheral T cell neoplasms, including T cell prolymphocytic leukemia, T-cell granular lymphocytic leukemia, aggressive NK-cell leukemia, cutaneous T cell lymphoma (mycosis fungoides/Sezary syndrome), anaplastic large cell lymphoma, T-cell type, enteropathy-type T cell lymphoma, Adult T-cell leukemia/lymphoma including those associated with HTLV-1, and angioimmunoblastic T cell lymphoma, and subcutaneous panniculitic T cell lymphoma; and (c) peripheral T cell lymphomas that initially involve a lymph node paracortex and never grow into a true follicular pattern. Other cancers to treat include hematologic malignancies, head and neck cancer, cancer of the gastrointestinal tract, ovarian cancer, and osteosarcoma.

In another embodiment, the present invention includes a method for treating inflammatory disorders comprising administering to a mammal suffering from said inflammatory disorder a therapeutically effective amount of a substantially pure diastereomer of 10-propargyl-10-deazaminopterin, or a salt, ester, solvate, and/or polymorph thereof, wherein the substantially pure diastereomer is (2S)-2-[[4-[(1S)-1-[(2,4-diaminopteridin-6-yl)methyl]but-3-ynyl]benzoyl]amino]pentanedioic acid or (2S)-2-[[4-[(1R)-1-[(2,4-diaminopteridin-6-yl)methyl]but-3-ynyl]benzoyl]amino]pentanedioic acid.

The term "inflammatory disorder" as used herein, refers to any disorder that is either caused by inflammation or whose symptoms include inflammation. By way of example, an inflammatory disorder caused by inflammation may be septic shock, and an inflammatory disorder whose symptoms include inflammation may be rheumatoid arthritis. The inflammatory disorders of the present invention include but are not limited to: cardiovascular disease, rheumatoid arthritis, multiple sclerosis, Crohn's disease, inflammatory bowel disease, systemic lupus erythematosis, polymyositis, septic shock, graft vs. host disease, asthma, rhinitis, psoriasis, and eczema. In one embodiment, an inflammatory disorder to treat includes rheumatoid arthritis and juvenile rheumatoid arthritis.

The terms "treatment," "treating" and "to treat" as used herein mean to alleviate symptoms, eliminate the causation of a cancer or an inflammatory disorder either on a temporary or a permanent basis, slow the appearance of symptoms and/or progression of the disorder, or prevent disease (i.e. to treat prophylactically). A subject receiving prophylactic treatment is generally a mammal at risk for a cancer or an inflammatory condition due to, for example, genetic predisposition, diet, exposure to disorder-causing agents, exposure to pathogenic agents, and the like.

The term "patient" or "mammal," as used herein, refers to any animal classified as a mammal, including humans, domestic and farm animals, and zoo or companion animals, such as dogs, horses, cats, cattle, etc. Preferably, the mammal is a human.

The PDX-10a and/or PDX-10b will typically be administered to the patient in a dose regimen that provides for the most effective treatment (from both efficacy and safety perspectives) for which the patient is being treated, as known in the art. In conducting the treatment method of the present invention, the PDX-10a and/or PDX-10b can be administered in any effective manner known in the art, such as by oral, topical, intravenous, intra-peritoneal, intramuscular, intra-articular, subcutaneous, intranasal, intra-ocular, vaginal, rectal, intracranial, or intradermal routes, depending upon the type of cancer being treated, and the medical judgment of the prescribing physician as based, e.g., on the results of published clinical studies.

The substantially pure PDX-10a or PDX-10b can be formulated as part of a pharmaceutical preparation. The specific dosage form will depend on the method of administration, but may include tablets, capsules, oral liquids, and injectable solutions for oral, intravenous, intramuscular, intracranial, or intraperitoneal administration, and the like. Dosing may be expressed as mg/m$^2$. Alternatively, dosing may be expressed as mg/kg body weight by any manner acceptable to one skilled in the art. One method for obtaining an equivalent dosing in mg/kg body weight involves applying the conversion factor 0.025 mg/kg, for an average human, as approximately equivalent to 1 mg/m$^2$. According to this calculation, dosing of 150 mg/m$^2$ is approximately equivalent to about 3.75 mg/kg.

Appropriate dosing for oncology for a diastereomer of the present invention includes the following dosage regimes. For example, doses on the order of 10 to 120 mg/m$^2$ of body surface area/day (about 0.25 to 3 mg/kg body weight per day) are appropriate. Dosages of 30 mg/m$^2$ (about 0.75 mg/kg) weekly for 3 weeks followed by a one week rest, 30 mg/m$^2$ (about 0.75 mg/kg) weekly×6 weeks followed by a one week rest, or gradually increasing doses of PDX on the weekly×6 week schedule are also suitable. Lower doses may be used as appropriate based on patient tolerance and type of malignancy. Higher doses can be utilized where less frequent administration is used. Thus, in a general sense, dosages of 10 to 275 mg/m$^2$ (about 0.25 to about 6.9 mg/kg) are suitably used with various dosing schedules, for example between about 100 to 275 mg/m$^2$ (about 2.5 to about 6.87 mg/kg) for biweekly dosages, and between about 10 to 150 mg/m$^2$ (about 0.25 to about 3.75 mg/kg), or, more specifically, between about 10 and 60 mg/m$^2$ for weekly dosages.

The determination of suitable dosages using protocols similar to those described in U.S. Pat. No. 6,323,205 is within the skill in the art. In one embodiment, the substantially pure PDX-10a or PDX-10b diastereomer can be administered in an amount of from about 10 to about 275 mg/m$^2$ (about 0.25 to about 6.87 mg/kg) per dose. Methods of the present invention also include administration of the substantially pure PDX-10a or PDX-10b diastereomer weekly; in a dose of about 10 mg/m$^2$ (0.25 mg/kg) or about 30 mg/m$^2$ (0.75 mg/kg); in an amount of from about 10 to about 150 mg/m$^2$ (about 0.25 to about 3.75 mg/kg) per dose; biweekly; and in a dosage amount of about 100 to about 275 mg/m$^2$ (about 2.5 to about 6.9 mg/kg). In one embodiment, the substantially pure PDX-10a or PDX-10b diastereomer can be administered in an amount of between about 0.25 mg/kg and about 4 mg/kg; between about 0.75 mg/kg and about 3 mg/kg; in an amount between about 1.0 mg/kg and about 2.5 mg/kg; in an amount of about 0.25 mg/kg or about 0.75 mg/kg (or an equivalent amount in body surface area (BSA)).

For treatment of an inflammatory disorder, substantially pure PDX-10a or PDX-10b diastereomer may be given by oral, intramuscular, intravenous, intra-arterial or intrathecal routes. Other routes will occur to those of skill in the art. For treatment of an inflammatory disorder, including, without limitation, psoriasis, rheumatoid arthritis, and/or juvenile rheumatoid arthritis, dosing can include the following. Methods of the present invention for adult rheumatoid arthritis or polyarticular-course Juvenile Rheumatoid Arthritis include oral administration of between about 1 and about 30 mg once weekly; in one embodiment, about 7.5 mg is administered once weekly. Other dosages may include 10 mg/m$^2$ given once weekly. Dosages may be adjusted gradually to achieve an optimal response. At higher dosages, such as over 20 mg/m$^2$/wk, or 0.65 to 1.0 mg/kg/wk, better absorption may be achieved by intramuscular or subcutaneous dosages. Appropriate dosing may also include 7.5 mg per week, or divided oral dosages of between about 0.5 and about 10 mg; in one embodiment, dosage may be divided oral dosage of 2.5 mg at 12 hour intervals for three doses given as a course once weekly. Dosing may be continued as long as it is effective, and includes therapy for up to two years and longer.

The substantially pure PDX-10a or PDX-10b diastereomer and other agents such as, for example, gemcitabine, erlotinib, a taxane, or bortezomib may be concurrently administered or utilized in combination as part of a common treatment regimen, in which the PDX-10a and/or PDX-10b and the other agent(s) are administered at the same or different times. In one embodiment of this invention, a pharmaceutical composition can comprise substantially pure PDX-10a or PDX-10b diastereomer in combination with an anticancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

For example, the other agent may be administered before, immediately afterward or after a period of time (for example 24 hours) relative to the administration of the substantially pure PDX-10a or PDX-10b diastereomer. Thus, for purposes of this application, the term administering refers generally to concurrent administration or to sequential administration of the drugs and in either order in a parallel treatment regimen with or without a separation in time between the drugs unless otherwise specified.

In one embodiment, substantially pure PDX-10a or PDX-10b can be administered at 2 mg/kg QD for five days, or two cycles of five days each, starting at the beginning of the treatment regimen.

Substantially pure PDX-10a or PDX-10b is suitably used in combination with folic acid and vitamin B12 supplementation to reduce the side effects of the treatment. For example, patients may be treated with folic acid (1 mg/m$^2$ daily starting 1 week prior to treatment with the substantially pure PDX-10a or PDX-10b diastereomer or alternatively 1 mg perioral (p.o.) daily not based on BSA); and B12 (1 mg/m$^2$ monthly, or alternatively given intramuscularly (I.M.) every 8-10 weeks as 1 mg (not based on BSA), or alternatively p.o. daily 1 mg (not based on BSA).

Substantially pure PDX-10a or PDX-10b can be administered in a wide variety of different dosage forms. For example, the substantially pure PDX-10a or PDX-10b can preferably be administered orally or parenterally. In one embodiment, the substantially pure PDX-10a or PDX-10b can be administered orally. In one embodiment, substantially pure PDX-10a or PDX-10b is administered parenterally, and may be administered via the intravenous route.

The substantially pure PDX-10a or PDX-10b can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, and others. Oral pharmaceutical compositions can be suitably sweetened and/or flavored. For oral administration of substantially pure PDX-10a or PDX-10b, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the substantially pure PDX-10a or PDX-10b may be combined with various sweetening or flavoring agents, coloring matter or dyes, and, if so desired, emulsifying and/or suspending agents as well, together with such diluents as water, ethanol, propylene glycol, glycerin and various like combinations thereof. A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 10 g of the active ingredient and each cachet or capsule preferably containing from about 0.05 mg to about 10 g of the active ingredient; tablets may also suitably contain about 2.5 mg active ingredient per tablet or about 7.5 mg per tablet.

For parenteral administration of substantially pure PDX-10a or PDX-10b, solutions may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

For veterinary purposes, the active agents can be administered separately or together to animals using any of the forms and by any of the routes described above. In a preferred embodiment, substantially pure PDX-10a or PDX-10b is administered in the form of a capsule, bolus, tablet, liquid drench, by injection or as an implant. As an alternative, the substantially pure PDX-10a or PDX-10b can be administered with the animal feedstuff, and for this purpose a concentrated feed additive or premix may be prepared for a normal animal feed. Such formulations are prepared in a conventional manner in accordance with standard veterinary practice.

The present invention further provides a kit comprising a single container comprising substantially pure PDX-10a or PDX-10b. In a preferred embodiment, the kit containers may further include a pharmaceutically acceptable carrier. The kit may further include a sterile diluent, which is preferably stored in a separate additional container. The kit may further include a package insert comprising printed instructions directing the use of the combined treatment as a method for treating cancer and/or inflammatory disorders.

Preferably the composition is comprised of a pharmaceutically acceptable carrier and a therapeutically effective amount of substantially pure PDX-10a or PDX-10b (including pharmaceutically acceptable salts esters, solvates, and polymorphs of each component thereof). Moreover, within this preferred embodiment, the invention encompasses a pharmaceutical composition for the treatment of disease, the use of which results in the inhibition of growth of neoplastic cells, benign or malignant tumors, or metastases, or treatment of inflammation, comprising a pharmaceutically acceptable carrier and a non-toxic therapeutically effective amount of substantially pure PDX-10a or PDX-10b (including pharmaceutically acceptable salts thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium salts. In one embodiment, the salt is the hydrochloride salt. Salts derived from pharmaceutically acceptable organic non-toxic bases also include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

In addition to the common dosage forms set out above, substantially pure PDX-10a or PDX-10b (including pharmaceutically acceptable salts, esters, solvates, and polymorphs of each component thereof) may also be administered by controlled release means and/or delivery devices.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing PDX-10a and/or PDX-10b (including pharmaceutically acceptable salts esters, solvates, and polymorphs of each component thereof) may also be prepared in powder or liquid concentrate form.

Dosage levels for the compounds of the combination of this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

In one aspect, the present invention includes pharmaceutical compositions of the present invention, for use in a method of treating cancer. The cancer to treat can be any of a number of cancers, as defined elsewhere herein, including, without limitation, prostate cancer, T-cell lymphoma, breast cancer, lung cancer, hematologic malignancies, head and neck cancer, cancer of the gastrointestinal tract, ovarian cancer, and osteosarcoma.

In one aspect, the present invention includes pharmaceutical compositions of the present invention, for use in treating an inflammatory disorder. An inflammatory disorder to treat can be any of a number of inflammatory disorders, as defined elsewhere herein, and includes, for example, rheumatoid arthritis.

In another aspect, the present invention includes the use of a compound according to the invention in the manufacture of a pharmaceutical composition for treating cancer. The cancer to treat can be any of a number of cancers, as defined elsewhere herein, including, without limitation, prostate cancer, T-cell lymphoma, breast cancer, lung cancer, hematologic malignancies, head and neck cancer, cancer of the gastrointestinal tract, ovarian cancer, and osteosarcoma.

In another aspect, the present invention includes the use of a compound according to the present invention in the manufacture of a pharmaceutical composition for treating an inflammatory disorder. An inflammatory disorder to treat can be any of a number of inflammatory disorders, as defined elsewhere herein, and includes, for example, rheumatoid arthritis. Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

The following examples are provided for illustrative purposes only and are not intended to limit the scope of the invention.

Example 1

Preparation of Racemic PDX

FIG. 1 shows a synthetic scheme useful in preparing 10-propargyl-10-dAM in accordance with the invention. A mixture of 60% NaH in oil dispersion (1.06 g, 26.5 mmol) in 18 mL of sieve-dried THF was cooled to 0° C. The cold mixture was treated with a solution of homoterephthalic acid dimethyl ester (5.0 g, 24 mmol. compound 1 in FIG. 1) in dry THF (7 mL), and the mixture was stirred for 1 hour at 0° C. Propargyl bromide (26.4 mmol) was added, and the mixture was stirred at 00° C. for an additional 1 hour, and then at room temperature for 16 hours. The resulting mixture was treated with 2.4 mL of 50% acetic acid and then poured into 240 mL of water. The mixture was extracted with ether (2.times.150 mL). The ether extracts were combined, dried over $Na_2SO_4$, and concentrated to an orange-yellow oil. Chromatography on silica gel (600 mL of 230-400 mesh) with elution by cyclohexane-EtOAc (8:1) gave the product α-propargylhomoterephthalic acid dimethyl ester (compound 2) as a white solid (4.66) which appeared by TLC (cyclohexane-EtOAc, 3:1) to be homogeneous. Mass spectral data on this product, however, showed it to be a mixture of the desired product 2, and the dipropargylated compound. No starting material 1 was detected. HPLC shows the ratio of mono- to di-propargylated products to be about 3:1. Since the dipropargylated product, unlike compound 1, cannot produce an unwanted coproduct in the next step of the reaction, this material was suitable for conversion to compound 3. Absence of starting compound 1 in the product used to proceed in the synthesis is preferable in order to avoid the sequential formation of 10-dAM during the transformations lading to the final product.

A mixture was formed by combining 0.36 g of a 60% NaH (9 mmol) in oil dispersion with 10 mL of dry DMF and cooled to 0-5° C. The cold mixture was treated drop-wise with a solution of the product of the first reaction (compound 2) (2.94 g, 12 mmol) in 10 mL dry DMF and then stirred at 0° C. for 30 minutes. After cooling to −25° C., a solution of 2,4, diamino-6-(bromomethyl)-pteridine hydrobromide-0.2 2-propanol (1.00 g, 2.9 mmol) in 10 mL dry DMF was added drop-wise while the temperature was maintained near −25° C. The temperature of the stirred mixture was allowed to rise to −10° C. over a period of 2 hours. After an additional 2 hours at −10° C., the temperature was allowed to rise to 20° C., stirring at room temperature was continued for 2 hours longer. The reaction was then adjusted to pH 7 by addition of solid $CO_2$, After concentration in vacuo to remove solvent, the residue was stirred with diethyl ether and the ether insoluble material was collected, washed with water, and dried in vacuo to give 1.49 g of a crude product. This crude product was dissolved in $CHCl_3$-MeOH (10:1) for application to a silica gel column. Elution by the same solvent system afforded 10-propargyl-10-carbomethoxy-4-deoxy-4-a-mino-10-deazapteroic acid methyl ester (compound 3) which was homogenous to TLC in 40% yield (485 mg).

A stirred suspension of compound 3 (400 mg, 0.95 mmol) in 2-methoxyethanol (5 mL) was treated with water (5 mL) and then 10% sodium hydroxide solution (3.9 mL). The mixture was stirred as room temperature for 4 hours, during which time solution occurred. The solution was adjusted to pH 8 with acetic acid and concentrated under high vacuum. The resulting residue was dissolved in 15 mL of water and acidified to pH 5.5-5.8 resulting in formation of a precipitate. The precipitate was collected, washed with water and dried in vacuo to recover 340 mg of compound 4 (91% yield). HPLC analysis indicated a product purity of 90%.

Compound 4 (330 mg) was decarboxylated by heating in 15 mL DMSO at 115-120° C. for 10 minutes. A test by HPLC after 10 minutes confirmed that the conversion was essentially complete. DMSO was removed by distillation in vacuo (bath at 40° C.). The residue was stirred with 0.5 N NaOH to give a clear solution, Acidification to pH 5.0 with 1N HCl gave 10-propargyl-4-deoxy-4-amino-10-deazapteroic acid (compound 5) as a yellow solid in 70% yield. HPLC indicated product purity at this stage as 90%.

Compound 5 (225 mg, 0.65 mmol) was coupled with dimethyl L-glutamate hydrochloride (137 mg, 0.65 mmol) using BOP reagent (benzotriazole-1-yloxytris(dimethylamino) phosphonium hexafluorophosphate (287 mg, 0.65 mmol, Aldrich Chemical Co.) in DMF (10 mL) containing triethylamine (148 mg, 1.46 mmol). The mixture was stirred for 3 hours at 20-25° C. and then evaporated to dryness. The residue was stirred with water, and the water-insoluble crude product was collected and dried in vacuo. The crude product (350 mg) was purified by silica gel chromatography with elution by $CHCl_3$-MeOH (10:1) containing triethylamine (0.25% by volume) to recover 165 mg of 10-propargyl-10-deazaminopterin dimethyl ester (compound 6, 50% yield) which was homogeneous to TLC ($CHCl_3$-MeOH 5:1).

Compound 6 (165 mg, 0.326 mmol) was suspended in 10 mL stirred MeOH to which 0.72 mL (0.72 meq) 1N NaOH was added. Stirring at room temperature was continued until solution occurred after a few hours. The solution was kept at 20-25° C. for 8 hours, then diluted with 10 mL water. Evaporation under reduced pressure removed the methanol, and the concentrated aqueous solution was left at 20-25° C. for another 24 hours. HPLC then showed the ester hydrolysis to be complete. The clear aqueous solution was acidified with acetic acid to pH 4.0 to precipitate 10-propargyl-10-deazaminopterin as a pale yellow solid, The collected, water washed and dried in vacuo product weighed 122 mg (79% yield). Assay by elemental analysis, proton NMR and mass spectroscopy were entirely consistent with the assigned structure. HPLC analysis indicated purity of 98% and established the product to be free of 10-deazaminopterin.

Example 2

Preparation of PDX-10a and PDX-10b Diastereomers

In order to prepare the diastereomers of the present invention, 225 g racemic compound 6 (prepared by the method shown in Example 1) was dissolved in the mobile phase (100% ethanol) at 3.1 g/l. Stirring and heating were used to dissolve the feed. The feed solution was filtered through a 0.2μ filter. Injection volume into the chiral column was 204 ml every 23 minutes with a large mid-cut being collected in order to ensure high chiral purity. Fractions collected were evaporated using a 20 L rotary evaporator at 40° C. and 50 mbar. Column was CHIRALPAK AD 20μ, 11 cm id×27 cm L (available from Daicel Chemical Industries Ltd., Japan); flow rate 400 ml/min, temperature 30° C., UV detection at 385 nm. Enantiomer purity was 97% or greater; determined by Chiralpak AD-H 4.6 mm ID×250 mm, using mobile phase 90/5/5 ethanol/methanol/isopropyl alcohol; 0.8 ml/min at 40° C., detection at 260 nm. Resolved Compound 6 (resolved into the R diastereomer at C10 (Peak 2) and the S diastereomer at C10 (Peak 1)) was then converted to the individual diastereomers of PDX (Compound 7) as PDX-10b and PDX-10a, respectively, by methods discussed in Example 1.

Example 3

$IC_{50}$ of Racemate and Diastereomers in Tumor Cell Lines

The agents PDX, PDX-10a, PDX-10b, were evaluated for growth inhibitory activity against, MDA-MB-435, SKBR-3 and NCI-H460 human tumor cell lines. Growth inhibition was measured by MTS assay following three hours of continuous treatment and a seventy-two hour recovery incubation. The purpose of these studies was to determine the cytotoxic activity of the compounds in the tumor cell lines studies studied.

Materials and Methods. Preparation of PDX-10a and PDX-10b was performed as discussed in Examples 1-2. The PDX compounds were diluted in dimethylsulfoxide (DMSO) at a concentration of 20 mM. From this solution a stock solution of 2 mM was made by dilution with phosphate-buffered saline (PBS). This 2 mM stock solution in 10% DMSO/90% PBS was used to make 2× concentrations of the titration series in cell growth medium which was added to the cell cultures in a 1:1 ratio to make 1× concentrations. Cell lines—The human tumor cell lines: MDA-MB-435 (melanoma), SKBR-3 (breast cancer) and NCI-H460 (lung cancer) were cultured in RPMI medium (RPMI; Nova Tech, Grand Island, N.Y.) containing ten percent dialyzed fetal bovine serum (FBS; Nova Tech). Once cells reached seventy percent confluency, they were trypsinized and resuspended in an alternate media (RPMI containing five percent dialyzed FBS (Hyclone, Logan, Utah). One day prior to treatment (Day 0), cultures were suspended at a concentration of $1-7.5\times10^4$ cell/ml and 100 µl aliquots were plated into each well of a 96-well microtiter plate at a final concentration of $1\times10^3-7.5\times10^3$ cells/well. Cells were incubated for 24 hours at 37° C. prior to exposure with agents.

Test Agents—racemic PDX, and individual diastereomers PDX-10a and PDX-10b were prepared as described above. Cells were treated 24 hours after plating (Day 1) with vehicle (media) alone or the above test agents for three hours at concentrations between 3 pM and 10 µM.

Single Agent Pulse Studies—Treatment with test agents or standard agents (controls) was initiated 24 hours after plating cells (Day 1). Cells were incubated at 37° C. with each of the test agents or a "chemococktail" (positive control) consisting of 215 µM Etoposide, 20 µM Taxol, 38.5 nM Velcade at final concentration for three hours. Following treatment, drug was removed, growth media added, and cells incubated at 37° C. for 72 hours. Following incubation, the viable cell number was quantified by the MTS assay described below. Experiments were repeated twice at the same concentrations. Results from these studies were used to calculate an $IC_{50}$ value (concentration of drug that inhibits cell growth by 50% of the vehicle) for each compound. $IC_{50}$ values were generated with Prizm software.

MTS Assay—Cell viability was determined using the MTS assay. This colorimetric procedure measures conversion of the MTS reagent (a tetrazolium salt) to formazan by living cells. Formazan production was quantified by spectrophotometric measurement at 490 nm and is proportional to viable cell number. For these studies, cells were cultured and treated as listed above. At the end of the treatment, 20 µl MTS tetrazolium (1.9 mg/ml in PBS, pH 6.0) was added to the cells for 1 hour at 37° C. Absorbance (OD) values were measured using a Dynex HD microplate reader at a single wavelength of 490 nm.

Data Analysis—Data from each experiment was collected and expressed as $OD_{490}$ versus the $\log_{10}$ of the test agent concentration. Using the statistical analysis package of the Prizm analytical software (GraphPad, San Diego, Calif.), a non-linear curve fit was performed which yielded the 50% inhibition concentration of the test article ($IC_{50}$).

Results and Discussion

Results and Discussion. The test agents racemic PDX, and diastereomers PDX-10a and PDX-10b, were tested on, MDA-MB-435, SKBR-3 and NCI-H460 human tumor cell lines using the MTS cell viability assay as described above. SKBR3 cells responded to racemic PDX, PDX-10a, and PDX-10b in a dose-dependent manner with an IC50 equal to 27.1, 11.9 and 26.1 nM, respectively.

MDA-MB435 cells responded in a dose-dependent manner to PDX, PDX-10a, and PDX-10b test agent with an IC50 value of 128.7, 100 and 120.6 nM, respectively.

NCI-H460 cells responded in a dose-dependent manner to PDX, PDX-10a, and PDX-10b test agent with an IC50 value of 100, 289 and 45.8 nM, respectively. In a repeat assay the IC50 values for PDX, PDX-10a, and PDX-10b were 124.3, 169.3, and 46.2 nM, respectively. Data for the CWR22-RV1 (prostate) cell lines were obtained in separate experiments, using methods as described herein, and are included in the table below.

| | PDX $IC_{50}$ (nM) | PDX-10a $IC_{50}$ (nM) | PDX-10b $IC_{50}$ (nM) |
|---|---|---|---|
| CWR22-RV1 (prostate) | 8.3 | 13.3 | 8.5 |
| SK-BR3 (breast) | 27.1 | 11.9 | 26.1 |
| MDA-MB-435 (melanoma) | 129 | 100 | 121 |
| NCI-H460 (lung) | 100 | 289 | 45.8 |
| NCI-H460 repeat | 124 | 169 | 46.2 |

IC50 = concentration resulting in half-maximal cytotoxic effect, nM = nanomolar.

Example 4

Pharmacokinetic Studies of PDX

Bioanalytical methods were developed and validated for quantitation of the 2 pralatrexate C10 diastereomers (PDX-10a and PDX-10b) in human, rat and dog plasma and urine. The basic bioanalytical method involves extraction of PDX-10a and PDX-10b from the matrix utilizing C18 solid-phase extraction (SPE) cartridges followed by derivatization (methylation with acetyl chloride) of the diastereomers for separation detection. The derivatized extracts are injected on a chiral high-performance liquid chromatography (HPLC) column for quantitation of each diastereomer by liquid chromatography-tandem mass spectrometry (LC/MS/MS). The lower limit of quantitation (LLOQ) for both diastereomers in plasma and urine matrices was 0.5 ng/mL.

Pharmacokinetic Parameters for Diastereomers: Nonclinical and clinical studies showed species-dependent differences in the clearance of the two pralatrexate C10 diastereomers (see Table below) with rats showing minimal differences and dogs showing 2-fold higher clearance of PDX-10b compared with PDX-10a. In humans, PDX-10b clearance was approximately 50% lower for both renal clearance ($CL_{ren}$) and nonrenal clearance ($CL_{nonren}$). The lower clearance and ~2-fold lower volume of distribution at steady state ($Vd_{ss}$) of PDX-10b are likely responsible for the 2-fold higher plasma exposure of PDX-10b compared with PDX-10a that is observed in humans. However, the plasma concentration-time profiles for both diastereomers declined in parallel, and terminal elimination half-life ($t_{1/2term}$) for both diastereomers was virtually identical. The biological cause for the observed stereoselectivity across species is unknown, but may be due to isomeric differences in plasma protein binding. Isomeric differences in tissue distribution and/or renal and hepatobiliary transport may contribute as well. In addition, data from in vitro studies in human hepatocytes and liver microsomes showed that the individual diastereomers were not subject to significant metabolism and did not interconvert.

Comparison of Racemic Pralatrexate Pharmacokinetic Parameters Across Species Upon Repeat Dosing

|  | Rat (PDX-T-07034-R) | | Dog (PDX-T-07054-D) | | Human (PDX-C1D6 or | |
|---|---|---|---|---|---|---|
|  | Day 1 | Day 85 | Day 1 | Day 281 | C1D1 | C2D6 |
| dose [mg/kg] | 5 | 5 | 0.7 | 0.7 | 0.81 | 0.81 |
| dose [mg/m$^2$] | 30 | 30 | 14 | 14 | 30 | 30 |
| $C_{max}$ [ng/mL]$^b$ | 19,245 | 14,257 | 1,793 | 649 | 5,815 | 4,963 |
| $AUC_\infty$ [ng/mL·min]$^b$ | 292,162 | 270,127 | 93,812 | 80,369 | 267,854 | 211,555 |
| $CL_{tot}$ [mL/min]$^c$ | 2.9-4.0 | 3.4-3.9 | 34-81 | 58-95 | 191-417 | 227-495 |
| $CL_{tot}$ relative to BW$^d$ [mL/min/kg] | ≈10 | ND | 4-10 | ND | 2-5 | ND |
| $Vd_{ss}$ [L]$^c$ | 0.07-0.89 | 0.15-0.18 | 8-16 | 15-24 | 37-105 | 48-162 |
| $Vd_{ss}$ relative to BW$^d$ [L/kg] | 0.2-2.5 | ND | 0.9-1.9 | ND | 0.4-1.2 | ND |
| $t_{1/2}^{term}$ [h]$^c$ | 1-20 | 1-6 | 4.4-4.9 | 4.7-5.5 | 12-18 | 11-16 |

$^a$Noncompartmental PK data from intense sampled patients (n = 10 [C1D1] and n = 6 [C1D6/C2D6])
$^b$Racemic mixture (PDX-10a + PDX-10b), males and females (mean)
Range of the mean observed for males and females and for PDX-10a and PDX-10b
Estimated values were calculated using average BW for males and females; 0.35 kg for rat, 8.5 kg for dog, and 85 kg for human (mean BW from PDX-008 noncompartmental PK population)
C = cycle,
D = dose,
mg = milligram,
kg = kilogram,
m$^2$ = square meter,
$C_{max}$ = maximum concentration,
ng = nanogram,
mL = milliliter,
$AUC_\infty$ = area under the curve to infinity,
min = minute,
$CL_{tot}$ = total clearance,
BW = body weight,
ND = not determined,
$Vd_{ss}$ = volume of distribution at steady state,
L = liter,
$t_{1/2}^{term}$ = terminal half-life,
h = hour Population (POP) pharmacokinetic (PK) parameters and effects of covariate factors (COV) for PDX-10a and PDX-10b after administration of racemic PDX in cancer patients were analyzed. POPPK data were pooled from 3 studies: 1) a phase 1 study in non-small lung cancer patients with intravenous (IV) doses of 150-325 mg/m$^2$, 2) a phase 1 study in advanced cancer patients with IV doses of 80-140 mg/m$^2$ plus a taxane, and 3) a phase 2 study in patients with relapsed or refractory PTCL at a dose of 30 mg/m$^2$/week IV. POP PK data for each diastereomer were analyzed using nonlinear mixed effects modeling with first-order conditional estimation. Model qualification included non-parametric bootstrap and predictive checks. Results: The POP PK database was comprised of 154 patients (94 males & 60 females, ages 21-85 years, weights 42.9-158 kg), contributing 1176 PDX-10a and 1173 PDX-10b plasma concentrations. POP PK data for PDX-10a & PDX-10b were described by 3-compartment (CMT) models parameterized as clearance (CL), volumes for CMT 1, 2, and 3, and 1$^{st}$ and 2$^{nd}$ inter-CMT CLs, with parameter estimates for PDX-10a: 35.0 L/hr, 11.0 L, 9.71 L, 50.6 L, 6.97 L/h, 1.43 L/h, and PDX-10b: 17.2 L/hr, 8.89 L, 6.79 L, 12.65 L, 5.53 L/h, and 0.601 L/h, respectively. PDX-10a and PDX-10b CL were reduced by 0.13 and 0.08 L/h per 1 mL/min reduction in creatinine clearance. Other COV findings were similar for both PDX-10a and PDX-10b.

Example 5

In Vitro Cytotoxicity Assays in Solid and Heme Cancer Cell Lines

Additional cancer cell lines can be tested in accordance with the methods outlined in Example 3. Cancer cell lines for T-cell lymphoma, multiple myeloma, hematologic malignancies, head and neck cancer, cancer of the gastrointestinal tract, ovarian cancer, and osteosarcoma are tested with PDX-10a and PDX-10b. The respective diastereomers have differential activity, PDX-10a showing increased activity relative to racemic PDX and/or PDX-10b in some cell lines, PDX-10b showing increased activity relative to racemic PDX and/or PDX-10a in other cell lines.

Example 6

In Vivo Xenograft Models with Solid Tumors and Lymphomas

Nude female mice are inoculated subcutaneously in the right flank with appropriate tumor cells as discussed in Example 5 to establish the xenotransplant. Tumor volume and body weights are monitored twice a week. Once the established tumor reaches 75-150 mm$^3$ the mice are randomized to a treatment group, either control, racemic PDX, PDX-10a, or PDX-10b. Treatments are administered by IP injection. Phosphate buffered saline is administered as control vehicles. The respective diastereomers can have differential activity, PDX-10a showing increased activity relative to racemic PDX and/or PDX-10b for some explants, PDX-10b showing increased activity relative to racemic PDX and/or PDX-10a for other explants.

Example 7

Antiarthritic Effect of Racemic PDX, PDX-10a and PDX-10b in Mammals

This example illustrates the antiarthritic activity of the diastereomeric compounds of the current invention in mammals. The study uses a mouse model of inflammatory disease that occurs in response to an antigenic challenge with Type II collagen according to method described in Nature, 283, 666-668 (1890). DBA/1 mice are immunized with a suspension of fetal bovine Type II collagen (1 mg/ml) prepared in complete Freund's adjuvant. The primary injection is given using 0.1 ml of the collagen emulsion giving a total of 0.1 mg of Type II collagen per mouse. The animals are given a booster injection of Type II collagen (100 μg in 0.01M acetic acid) on day 21 by intraperitoneal injection.

In vivo testing of racemic PDX, PDX-10a and PDX-10b can show that using prophylactic regimens in which drug administration is initiated two days prior to administration of antigen (Type II collagen) is more effective than starting drug at day 19, two days prior to the first and only boost with Type II collagen. In this model the untreated positive control animals may have an incidence of arthritis ranging from 90% to 100% of injected animals at day 44. The effect of methotrexate and test compounds racemic PDX, PDX-10a and PDX-10b on the extent of inflammation is determined by visual observation and by direct analysis of paw swelling using caliper measurements. A direct correlation may exist between the decrease in the number of animals having disease and a decrease in the extent of inflammation, as determined by paw swelling. The respective diastereomers have differential activity, PDX-10a showing increased activity relative to racemic PDX and/or PDX-10b for some components/aspects of the arthritis, and PDX-10b showing increased activity relative to racemic PDX and/or PDX-10a for other components/aspects of the arthritis.

The antiinflammatory activity of methotrexate is accepted as an effective comparative standard for determination of the antiinflammatory activity of other compounds. The respective diastereomers can have differential activity, PDX-10a showing increased activity relative to racemic PDX and/or PDX-10b for some components/aspects of the arthritis, and PDX-10b showing increased activity relative to racemic PDX and/or PDX-10a for other components/aspects of the arthritis.

Example 8

Antiarthritic Effect of Racemic PDX, PDX-10a and PDX-10b in Mammals

Female Lewis rats with 17-day developing type II collagen arthritis are treated once daily (qd), orally or intravenously, on days 0-16 of the study with saline vehicle (qd), with Methotrexate (MTX, 0.075, 0.05, or 0.025 mg/kg), or racemic PDX, PDX-10a and PDX-10b (0.075, 0.05, or 0.025 mg/kg). Animals are terminated on study day 17. Efficacy evaluation is based on ankle caliper measurements, expressed as area under the curve (AUC), and terminal hind paw weights, and histopathologic evaluation of ankles and knees. All animals survive to termination of study.

Inhibition of ankle diameter can be seen in rats treated po, qd with certain doses of MTX, racemic PDX, PDX-10a and PDX-10b. Inhibition of ankle diameter AUC may be significant for rats treated p.o., q.d. with certain doses of MTX, racemic PDX, PDX-10a and PDX-10b. Inhibition of final paw weight may be significant for rats treated po, qd with MTX, racemic PDX, PDX-10a and PDX-10b. The anti-inflammatory activity of methotrexate is accepted as an effective comparative standard for determination of the anti-inflammatory activity of other compounds. The respective diastereomers may have differential activity, PDX-10a showing increased activity relative to racemic PDX and/or PDX-10b for some components/aspects of the arthritis, and PDX-10b showing increased activity relative to racemic PDX and/or PDX-10a for other components/aspects of the arthritis.

Example 9

Oral Formulation—Tablets

Each tablet contains PDX-10a and/or PDX-10b sodium (active ingredient) in an amount equivalent to the labeled amount of substantially pure PDX-10a or PDX-10b, and contains the following inactive ingredients: anhydrous lactose, crospovidone, hydroxypropyl methylcellulose, magnesium stearate, microcrystalline cellulose, polyethylene glycol, polysorbate 80, pregelatinized starch, sodium carbonate monohydrate, talc and titanium dioxide. Amounts of active ingredient per tablet are 2.5 mg, 5 mg, 7.5 mg, or 10 mg.

The active ingredient is blended with the other ingredients until a uniform blend is formed. One or more of the other ingredients is blended with water to form a paste. This is then mixed until uniform granules are obtained. The granules are screened through a suitable milling machine using a ¼" stainless steel screen. The milled granules are dried in a suitable drying oven and milled through a suitable milling machine again. The resulting mixture is compressed into tablets of desired shape, thickness, hardness and disintegration.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. A method for treating an inflammatory disorder in a mammal, comprising administering to a mammal in need of said treatment a therapeutically effective amount of a diastereomer of 10-propargyl-10-deazaaminopterin, or a pharmaceutically acceptable salt thereof, said diastereomer being (2S)-2-[[4-[(1R)-1-[(2,4-diaminopteridin-6-yl)methyl]but-3-ynyl]benzoyl]amino]pentanedioic acid.

2. The method according to claim 1, wherein the diastereomer is administered orally.

3. The method according to claim 2, wherein the oral dosage is between 1 mg and 30 mg per dose.

4. The method according to claim 1, wherein the diastereomer is administered via intravenous administration.

5. The method according to claim 4, wherein the dosage is between 30 to 150 mg/m$^2$ per dose.

6. The method according to claim 1, wherein the diastereomer is (2S)-2-[[4-[(1R)-1-[(2,4-diaminopteridin-6-yl)methyl]but-3-ynyl]benzoyl]amino]pentanedioic acid in an amount greater than 90% by weight of the total amount of 10-propargyl-10-deazaaminopterin.

7. The method according to claim 1, wherein the pharmaceutically acceptable salt thereof is a sodium salt.

8. The method of claim 1, wherein the inflammatory disorder is rheumatoid arthritis.

* * * * *